United States Patent [19]

Landler

[11] 4,181,805

[45] Jan. 1, 1980

[54] PROCESS FOR THE PREPARATION OF PURE SODIUM HYDROXIDE ADDITION COMPOUNDS OF CIS-ISOMERS OF NAPHTHOYLENE-BIS-BENZIMIDAZOLES

[75] Inventor: Josef Landler, Hofheim am Taunus, Fed. Rep. of Germany

[73] Assignee: Hoechst Aktiengesellschaft, Frankfurt am Main, Fed. Rep. of Germany

[21] Appl. No.: 17,937

[22] Filed: Mar. 6, 1979

[30] Foreign Application Priority Data

Mar. 8, 1978 [DE] Fed. Rep. of Germany ....... 2809877

[51] Int. Cl.$^2$ ............................................. C07D 235/20
[52] U.S. Cl. ..................................................... 548/328
[58] Field of Search ......................................... 548/328

[56] References Cited

U.S. PATENT DOCUMENTS

| | | | |
|---|---|---|---|
| 3,072,661 | 1/1963 | Pizzarello et al. | 546/32 |
| 3,641,051 | 2/1972 | Frischkorn et al. | 548/328 |

FOREIGN PATENT DOCUMENTS

| | | | |
|---|---|---|---|
| 567210 | 12/1932 | Fed. Rep. of Germany | 548/328 |
| 852725 | 10/1952 | Fed. Rep. of Germany | 548/328 |
| 1569736 | 7/1970 | Fed. Rep. of Germany | 548/328 |
| 1237838 | 6/1971 | United Kingdom | 548/328 |

*Primary Examiner*—Natalie Trousof
*Attorney, Agent, or Firm*—Curtis, Morris & Safford

[57] ABSTRACT

The pure sodium hydroxide addition products of the cis-isomers of naphthoylene-bis-benzimidazoles are recovered from their alkaline aqueous-alcoholic solution as obtained in their synthesis by eliminating the alcohol as far as feasible, reacting the remaining aqueous alkaline solution with chlorine or sodium hypochlorite solution at an elevated temperature, removing the insoluble by-products, introducing into the hot solution a compound yielding sodium ions and isolating the precipitating product or processing it further to yield the free naphthoylene-bis-benzimidazole pigments.

14 Claims, No Drawings

PROCESS FOR THE PREPARATION OF PURE SODIUM HYDROXIDE ADDITION COMPOUNDS OF CIS-ISOMERS OF NAPHTHOYLENE-BIS-BENZIMIDAZOLES

The present invention relates to a process for the preparation of pure sodium hydroxide addition compounds of cis-isomers of naphthoylene-bis-benzimidazoles.

The invention provides a process for the preparation of pure sodium hydroxide addition compounds of the cis-isomers of naphthoylene-bis-benzimidazoles from an aqueous-alcoholic alkaline solution with separation of the alcohol, which comprises removing the alcohol to a high degree, treating the aqueous-alkaline solution with chlorine at a temperature of up to 90° C., then separating insoluble by-products, introducing a compound yielding sodium ions into the hot solution, and isolating the precipitating addition product or immediately processing the same.

From German Pat. No. 567,210 it is already known that the cis-trans-isomers obtained in the condensation of naphthalene-1,4,5,8-tetracarboxylic acid with o-phenylene-diamine show great differences in their solubility, so that a simple separation may be effected. For this purpose the condensation product is heated with potassium hydroxide and ethanol, in which process the cis-compound is dissolved. After separating the insoluble trans-addition product, the cis-isomer is precipitated from the filtrate with water. It has also been mentioned that instead of potassium hydroxide there may be used sodium hydroxide.

In German Pat. No. 1,569,736 it is described that the pure isomers of naphthoylene-bis-benzimidazoles may be obtained in a single operation step, if naphthalene-1,4,5,8-tetracarboxylic acid or the anhydrides thereof are condensed with 1,2-diaminobenzene in low-boiling alcohols at a temperature of from 120° to 180° C. under pressure, and if the isomer mixture formed is converted in the same medium by a treatment with alkalis into the alkali addition compounds which are then separated from one another by filtration due to their different solubility. As alkalis there are mentioned above all sodium or potassium hydroxide. In the example it has been mentioned that the dyestuff obtained from the alcoholic mother and washing liquor is produced in a purer form, if at first part of the ethanol used is distilled off from the combined mother liquors, the precipitated potassium addition compound is filtered off with suction and is subsequently hydrolyzed in warm water.

From U.S. Pat. No. 3,072,661 it is known to largely eliminate the alcohol from the aqueous-ethanolic alkaline mother liquors by distillation, until the content of alcohol is only about 20% by weight, to replace the volume distilled off by water, to clarify the solution thus obtained with filtering auxiliaries, to precipitate the cis-isomer with 6 to 12 times the amount by weight, calculated on the cis-isomer, of p-toluene-sulfonic acid, to heat the suspension subsequently at first to about 55° C., thereafter to 75° to 90° C., and then to separate the product obtained in pigmentary form.

In all of these known processes the purity of the product obtained is not yet satisfactory. The impurities contained in the products become evident in a more or less strong dulling of the shade and also in a deterioration of the fastness properties, especially the fastness to migration and above all the fastness to solvents and to overvarnishing (overlacquering).

It has now been found that the products purified according to the invention are superior to the known products, both when being used as vat dyes on cotton and in the form of pigments. Thus, the colorants obtained in accordance with the invention are marked by a very pure shade, a higher tinctorial strength, as well as by improved fastness properties.

In the following, some preferred embodiments of the invention are illustrated in detail: The alcohol, generally ethanol, is separated from the aqueous-alcoholic alkaline solutions as far as it is technically feasible and reasonable, since the remaining alcohol requires a higher chlorine consumption which, in turn, yields more undesired chlorides which must be removed from the effluents.

Instead of a treatment with chlorine gas, there may also be employed the so-called "chlorine bleaching liquor" (sodium hypochlorite solution), as the process is carried out in the aqueous-alkaline medium.

The oxidizing treatment is preferably carried out at a temperature in the range of from about 20° to 60° C., in which process chlorine is at first added in the same rate as it is consumed. The reaction mixture is suitably stirred with a slight excess amount of chlorine for some time, for example 30 minutes, at a temperature in the range of from 55° to 65° C. or at a slightly elevated temperature, and subsequently the reaction mixture is brought to an elevated temperature, whereupon the remaining chlorine is consumed.

The insoluble products formed in the oxidation process are separated, suitably by filtering off following the addition of clarifying auxiliaries. As clarifying auxiliaries there may be mentioned, for example, bleaching earths and/or charcoal.

As compounds yielding sodium ions there are suitable sodium hydroxide and/or sodium salts, and for economical reasons especially sodium chloride or sodium sulfate, as well as salt mixtures. Since the precipitation of the sodium hydroxide addition compound, which is less soluble than the potassium hydroxide compound, is intended, the amount of the compound added which yields sodium ions depends on the concentration of potassium and sodium ions already present. The sodium ion concentration required for the complete precipitation of the sodium hydroxide addition compound may easily be determined by a simple preliminary test. The compound yielding sodium ions is introduced into the hot clarified filtrate, preferably in a solid form, optionally also as a highly concentrated solution. The sodium hydroxide addition compound separates upon cooling in a well crystallized form.

If the sodium hydroxide addition compound is to be isolated, it may also be freed from the adherent mother liquor—depending on the desired degree of purity—by washing with concentrated sodium hydroxide solution. The product thus obtained may then be converted, for example, into a pigment preparation, while the preparation agent is already present when the pigment grain is set free by the hydrolysis of the sodium hydroxide addition compound (e.g. conversion into a wax preparation as described in U.S. patent application Ser. No. 949,632, filed Nov. 3, 1978).

It is also possible to hydrolyze the sodium hydroxide addition compound without isolation immediately with water or diluted acid. Depending on the required purity of the product, the sodium hydroxide addition compound may be washed with concentrated sodium hydroxide solution or, for example, only be suction-dried to a large extent.

The purification process of the invention is suitable not only for the unsubstituted cis-naphthoylene-bis-benzimidazole, but also for the derivatives thereof which are sufficiently stable to the oxidative process of the invention, e.g. the halogenated, especially chlorinated derivatives.

The following Examples serve to illustrate the invention, the percentages being by weight.

EXAMPLE 1

The isomer mixture obtained from the condensation of 100 parts by weight of naphthalene-1,4,5,8-tetracarboxylic acid anhydride with 76 parts by weight of 1,2-diaminobenzene is treated with potassium hydroxide in an ethanol/water mixture at boiling temperature, in order to separate the two isomers according to German Pat. No. 1,569,736 (U.S. Pat. No. 3,865,829). Upon formation of the sparingly soluble KOH compound of the trans-isomer, the latter compound is separated by filtration.

From the filtrate containing the cis-isomer, the total amount of ethanol is distilled off. 20 Parts by weight of gaseous chlorine are introduced into the remaining distillation residue, while stirring and starting at 20° C., whereupon the temperature rises to 50°-60° C. Thereafter 380 parts by weight of hot water are added to the mixture and 6 parts by weight each of bleaching earth and charcoal are introduced. The reaction mixture is stirred for another 30 minutes at 90° C. and is then filtered while still hot. 80 Parts by weight of solid sodium hydroxide are stirred into the hot filtrate. After the solid matter has been dissolved, stirring is discontinued and the mixture is cooled to 20° C., in order to allow the pure cis-isomer of the NaOH addition compound to crystallize. The precipitate is then isolated on a suction-filter, and the adherent mother liquor is wahsed out with 25% sodium hydroxide solution.

EXAMPLE 2

The process is at first carried out as has been described in Example 1. After the isolation of the ethanol-free distillation residue the oxidation is effected by using 340 parts by weight of chlorine bleaching liquor (13% of active chlorine) instead of chlorine, in which process only 60 parts by weight of hot water are added. The isolated NaOH addition compound as well as the cis-naphthoylene-bis-benzimidazole obtained thereof by way of hydrolysis are identical with the products which can be obtained in accordance with Example 1.

EXAMPLE 3

The oxidation and the separation of the sparingly soluble impurities are carried out as has been described in Example 1. 20 Parts by weight of sodium hydroxide are added to the hot clear filtrate, and after the dissolution of the former, 60 parts by weight of sodium chloride (in solid form or as a 30% aqueous solution) are introduced by stirring. The process is then followed up as has been described in Example 1. The isolated sodium hydroxide addition compound as well as the cis-naphthoylene-bis-benzimidazole obtained thereof by way of hydrolysis show the same quality as the products obtained according to Example 2.

EXAMPLE 4

The oxidation is carried out as has been described in Example 2. After the separation of the impurities and clarifying agents, 200 parts by weight of a 30% aqueous sodium chloride solution are added to the clear solution. The process is then followed up as has been indicated in Example 1.

The isolated sodium hydroxide addition compound as well as the cis-naphthoylene-bis-benzimidazole obtained thereof by hydrolysis show the same quality as the products obtained according to Example 2.

The following Example describes the conversion of a sodium hydroxide addition compound into a vat dyestuff.

EXAMPLE 5

400 Parts by weight of the sodium hydroxide addition compound obtained according to Example 1 are stirred into 2 liters of water, and stirring is continued for 2 hours at a temperature of from 70° to 80° C., in order to facilitate the filtration. The precipitated dyestuff is isolated on a suction-filter, washed with water until neutral and dried.

The pure cis-naphthoylene-bis-benzimidazole thus obtained shows as vat dyestuff on cotton a considerably higher tinctorial strength and purity than a product obtained according to the state of the art.

The following Examples describe the method according to which a sodium hydroxide addition compound may be converted into a pigment preparation.

EXAMPLE 6

455 Parts by weight of the cis-isomer of the sodium hydroxide addition compound of the naphthoylene-bis-benzimidazole having a content of 22% of pure pigment are introduced, while stirring vigorously, into a previously prepared mixture of 5° C. consisting of 2 liters of water, in which a solution of 5 parts by weight of a polyethylene wax (molecular weight about 2000, non-emulsifiable, dropping point: 103° to 107° C., solidification point: 90° to 94° C., acid and saponification number: 0, density at 20° C.: 0.91 to 0.92) in 20 parts by weight of chlorobenzene has been stirred thoroughly. The pigment suspension is continued to be stirred for 3 hours at room temperature. Subsequently it is heated to a temperature of from 70° to 75° C., and stirring is continued at this temperature for another 2½ to 3 hours. Thereafter the chlorobenzene is distilled off with steam, the pigment is isolated on a suction-filter, washed with water until neutral and dried in a drying cabinet with air circulation at 80° to 90° C. Yield: 105 Parts by weight of pigment preparation.

The pigment dried to become chalky and soft can easily be ground. The excellent dispersibility of this pigment preparation allows its use in a wide range of applications. The excellent pigment distribution and tinctorial strength become especially evident on dyeing polyolefins in the mass.

EXAMPLE 7

455 Parts by weight of the cis-isomer of the sodium hydroxide addition compound of naphthoylene-bis-benzimidazole containing 22% of pure pigment are introduced, while stirring vigorously, into a previously prepared mixture of 5° C. consisting of 2 liters of water in which a solution of 5 parts by weight of the wax described in Example 6 in 20 parts by weight of chlorobenzene has been stirred thoroughly. The pigment suspension is stirred for another 3 hours at room temperature. Thereafter the suspension is heated to 70°–75° C., and stirring is continued at this temperature for another 2½ hours. Subsequently the suspension is filtered off with suction, the chlorobenzene adhering to the preparation is washed out with ethanol, whereupon the filtered product is washed with water until neutral. The drying is effected at 80° to 90° C. in a drying cabinet with air circulation. Yield: 105 Parts by weight of pigment preparation.

The pigment preparation thus isolated is identical with the product obtained according to Example 6.

What is claimed is:

1. A process for obtaining a pure sodium hydroxide addition product of the cis-isomer of a naphthoylene-bis-benzimidazole from its aqueous-alcoholic alkaline solution, which comprises removing the alcohol, reacting the remaining essentially aqueous alkaline solution with chlorine gas or an alkali metal hypochlorite at a temperature between room temperature and about 90° C., removing insoluble by-products and adding to the remaining solution an amount of a compound yielding sodium ions sufficient to precipitate said addition product.

2. A process as claimed in claim 1, wherein the naphthoylene-bis-benzimidazole is unsubstituted or substituted by substituents stable towards oxidation with chlorine in an aqueous-alkaline medium.

3. A process as claimed in claim 2, wherein the benzo nuclei of the naphthoylene-bis-benzimidazole are substituted by 1 or 2 chlorine atoms.

4. A process as claimed in claim 1, wherein the alcohol in the starting solution is a lower alkanol.

5. A process as claimed in claim 4, wherein the alcohol is methanol or ethanol.

6. A process as claimed in claim 1, wherein the chlorine or hypochlorite is added at such a rate as it is consumed.

7. A process as claimed in claim 1, wherein the chlorine or hypochlorite is added at a temperature of about 20° to about 60° C.

8. A process as claimed in claim 7, wherein the reaction mixture containing a slight excess of chlorine or hypochlorite is heated to a higher temperature until the chlorine or hypochlorite is consumed.

9. A process as claimed in claim 1, wherein the hypochlorite is sodium hypochlorite.

10. A process as claimed in claim 9, wherein the sodium hypochlorite is added in the form of a sodium hypochlorite bleach liquor.

11. A process as claimed in claim 1, wherein the compound yielding sodium ions is sodium hydroxide or an inorganic sodium salt.

12. A process as claimed in claim 11, wherein the salt is the chloride, sulfate or a mixture of these salts or one of these salts with another sodium salt.

13. A process as claimed in claim 11, wherein the sodium hydroxide is added in solid form.

14. A process as claimed in claim 1, wherein the insoluble by-products are removed by means of a filter aid.

* * * * *